(12) United States Patent
Sabelle et al.

(10) Patent No.: US 7,435,268 B2
(45) Date of Patent: *Oct. 14, 2008

(54) N-ALKYLHYDROXYLATED SECONDARY PARA-PHENYLENEDIAMINE COMPOUNDS, COMPOSITION FOR DYEING KERATIN FIBERS COMPRISING THE SAME, AND DYEING PROCESSES USING THE COMPOSITION

(75) Inventors: Stéphane Sabelle, Paris (FR); Eric Metais, St-leu-le-Foret (FR)

(73) Assignee: L'Oreal S.A., Paris (FR)

( * ) Notice: Subject to any disclaimer, the term of this patent is extended or adjusted under 35 U.S.C. 154(b) by 68 days.

This patent is subject to a terminal disclaimer.

(21) Appl. No.: 11/066,532

(22) Filed: Feb. 28, 2005

(65) Prior Publication Data

US 2006/0005322 A1    Jan. 12, 2006

Related U.S. Application Data

(60) Provisional application No. 60/568,665, filed on May 7, 2004.

(30) Foreign Application Priority Data

Feb. 27, 2004   (FR) .................................. 04 02018

(51) Int. Cl.
*A61Q 5/10* (2006.01)
*C07C 211/00* (2006.01)

(52) U.S. Cl. ...................... 8/405; 8/406; 8/407; 8/408; 8/410; 8/415; 8/421; 564/388; 564/389

(58) Field of Classification Search ...................... 8/405, 8/406, 407, 408, 410, 414, 415, 421; 564/387, 564/388, 389
See application file for complete search history.

(56) References Cited

U.S. PATENT DOCUMENTS

| | | | |
|---|---|---|---|
| RE30,199 E | 1/1980 | Rose et al. | |
| 4,330,291 A | 5/1982 | Bugaut et al. | |
| 4,745,652 A | 5/1988 | Rose et al. | |
| 4,823,985 A | 4/1989 | Grollier et al. | |
| 5,061,289 A | 10/1991 | Clausen et al. | |
| 5,096,455 A | 3/1992 | Grollier | |
| 5,167,669 A | 12/1992 | Grollier | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,766,576 A | 6/1998 | Lowe et al. | |
| 6,004,356 A * | 12/1999 | Audousset | 8/412 |
| 6,099,592 A | 8/2000 | Vidal et al. | |
| 6,284,003 B1 | 9/2001 | Rose et al. | |
| 6,565,614 B1 * | 5/2003 | Genet et al. | 8/406 |
| 6,630,004 B1 * | 10/2003 | Philippe et al. | 8/409 |
| 6,645,258 B2 | 11/2003 | Vidal et al. | |
| 6,730,789 B1 | 5/2004 | Birault et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 714 954 A2 | 6/1996 |
| EP | 0 770 375 B1 | 5/1997 |
| EP | 1 093 790 A2 | 4/2001 |
| FR | 2 586 913 A1 | 3/1987 |
| FR | 2 649 886 A1 | 1/1991 |
| FR | 2 733 749 A1 | 11/1996 |
| FR | 2 801 308 A1 | 5/2001 |
| GB | 1026978 | 4/1966 |
| GB | 1153196 | 5/1969 |
| JP | 2-19576 A | 1/1990 |
| JP | 05-163124 | 6/1993 |
| WO | WO 94/08969 A1 | 4/1994 |
| WO | WO 94/08970 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WO 99/03819 A1 | 1/1999 |

OTHER PUBLICATIONS

STIC Search Report dated Mar. 22, 2007.*
Kotsuki et al., "High Pressure Organic Chemistry: XII. A Convenient Synthesis of Aromatic Amines from Activated Aromatic Fluorides," Synthesis, vol. 12, pp. 1147-1148 (1990).
Massa et al., "Spiro-4H-pyrrolo[1,2-a][1,4]benzodiazephine-4,4'piperidine] derivatives as potential nootropic agents: A simple one-pit synthesis," Synth. Commun., vol. 20, No. 22, pp. 3537-3543 (1990).

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to novel N-alkylhydroxylated secondary para-phenylenediamines and a process for making these compounds. The present disclosure further relates to a composition for dyeing keratin fibers, including human keratin fibers such as hair, containing, in a medium that is suitable for dyeing, at least one such N-alkylhydroxylated secondary para-phenylenediamine, a process for dyeing keratin fibers using the composition, and a device or kit for dyeing keratin fibers that contains the composition.

27 Claims, No Drawings

OTHER PUBLICATIONS

French Search Report for FR 04 02018 (Priority Application for U.S. Appl. No. 11/006,532), filed Sep. 29, 2004, Ex. Bedel.

English language Derwent Abstract of EP 0 770 375 A1, May 2, 1997.

English language Derwent Abstract of EP 1 093 790 A2, Apr. 25, 2001.

English language Derwent Abstract of JP 02-19576 A, Jan. 23, 1990.

English language Derwent Abstract of JP 05-163124, Jun. 29, 1993.

* cited by examiner

N-ALKYLHYDROXYLATED SECONDARY PARA-PHENYLENEDIAMINE COMPOUNDS, COMPOSITION FOR DYEING KERATIN FIBERS COMPRISING THE SAME, AND DYEING PROCESSES USING THE COMPOSITION

CROSS-REFERENCE TO RELATED APPLICATIONS

This application claims benefit of U.S. Provisional Application No. 60/568,665, filed May 7, 2004, and French Application No. 04/02018, filed Feb. 27, 2004, both of which are incorporated herein by reference.

FIELD OF THE INVENTION

The present disclosure relates to a novel family of N-alkylhydroxylated secondary para-phenylenediamines and to their use for dyeing keratin fibers, including human keratin fibers such as hair.

BACKGROUND OF THE INVENTION.

It is known practice to dye keratin fibers, such as human hair, with dye compositions containing oxidation dye precursors, such as ortho- or para-phenylenediamines, ortho- or para-aminophenols, and heterocyclic compounds, which are generally referred to as oxidation bases. These oxidation bases, can be colorless or weakly colored compounds which, when combined with oxidizing products, may give rise to colored compounds by a process of oxidative condensation.

It is also known that the shades obtained with these oxidation bases may be varied by combining them with couplers or coloration modifiers, which may be chosen from aromatic meta-diaminobenzenes, meta-aminophenols, meta-diphenols and certain heterocyclic compounds such as indole compounds.

The variety of molecules that can be used as oxidation bases and couplers makes it possible to obtain a wide range of colors.

The "permanent" coloration obtained by means of these oxidation dyes should, moreover, satisfy a certain number of requirements. Thus, it should not have toxicological drawbacks, it should allow shades of the desired intensity to be obtained, and it should have good resistance to external agents such as light, bad weather, washing, permanent waving, perspiration and rubbing.

The dyes may also allow white hairs to be covered and, lastly, they may be as unselective as possible, that is to say that they may allow the smallest possible differences in coloration to be produced over the entire length of the same keratin fiber, which is generally differently sensitized (e.g., damaged) between its end and its root.

SUMMARY OF THE INVENTION

The present inventor has discovered, surprisingly and advantageously, that it is possible to obtain novel compositions for dyeing keratin fibers, including human keratin fibers such as hair, which are capable of giving strong, aesthetic, unselective colorations in varied shades, which show good resistance to the various attacking factors to which the fibers may be subjected, by using at least one N-alkylhydroxylated secondary para-phenylenediamine.

In addition, these compositions have a good toxicological profile.

A first aspect of the present disclosure relates to a family of N-alkylhydroxylated secondary para-phenylenediamines, to processes for synthesizing them and to their uses, including dyeing keratin fibers such as human hair.

Another aspect of the present disclosure relates to compositions containing at least one N-alkylhydroxylated secondary para-phenylenediamine, dyeing processes using these compositions, and a multi-compartment device or dyeing "kit" containing such compositions.

The composition as disclosed herein makes it possible to obtain very strong, unselective coloration of keratin fibers that is resistant with respect to external agents, such as light, while at the same time avoiding the degradation of the fibers.

Other aspects and benefits of the present disclosure will emerge even more clearly on reading the description and the non-limiting examples that follow.

In the present disclosure, the term "alkyl" means a linear or branched $C_1$-$C_{14}$ radical, such as the following non-limiting examples of linear or branched radicals: methyl, ethyl, propyl, butyl, pentyl, hexyl, octyl, at the like.

DETAILED DESCRIPTION OF THE INVENTION

The novel N-alkylhydroxylated secondary para-phenylenediamines according to the present disclosure are compounds of formula (I):

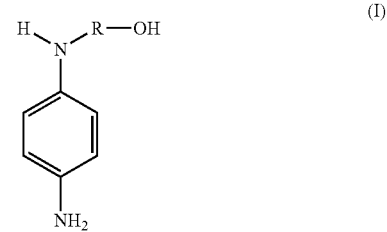

wherein:

R is a linear or branched $C_2$-$C_{14}$ alkylene radical substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5- or 6-membered heterocycles; or R is a linear or branched $C_2$-$C_{14}$ alkylene radical, comprising one or more atoms chosen from nitrogen and oxygen, and optionally substituted with one or more groups chosen from amino, monoalkylamino, dialkylamino, alkylcarbonyl, amido, monoalkylaminocarbonyl, dialkylaminocarbonyl, and saturated 5- or 6-membered heterocycles, with the proviso that the compound of formula (I) is not 4-amino-N-[β-(β'-hydroxyethoxy)ethyl]aniline.

According to one embodiment of the present disclosure, the radical R is a linear or branched $C_2$-$C_8$ alkylene radical, such as a linear or branched $C_2$-$C_6$ alkylene radical, substituted with a group chosen from $C_1$-$C_{10}$ alkoxy, amino, $C_1$-$C_3$ monoalkylamino, $C_1$-$C_3$ dialkylamino, amido, di($C_1$-$C_3$) alkylaminocarbonyl, and saturated 5- or 6-membered heterocycles comprising a nitrogen atom.

According to another embodiment of the present disclosure, the radical R is a linear $C_2$-$C_6$ alkylene radical comprising one or two atoms chosen from nitrogen and oxygen.

In yet another embodiment of the present disclosure, the radical R is a linear or branched $C_2$-$C_8$ alkylene radical, such as a linear or branched $C_2$-$C_6$ alkylene radical, comprising one or more atoms chosen from nitrogen and oxygen, and substituted with a group chosen from $C_1$-$C_3$ alkylamino and $C_1$-$C_3$ dialkylamino, and saturated 5- or 6-membered heterocycles comprising a nitrogen atom.

The compounds of formula (I) may be in free form or in the form of salts, such as the addition salts with an acid, which may be chosen from the hydrochlorides, hydrobromides, sulfates, citrates, succinates, tartrates, lactates, tosylates, benzenesulfonates, phosphates and acetates.

Mention may be made of the following non-limiting examples of compounds of formula (I) chosen from:

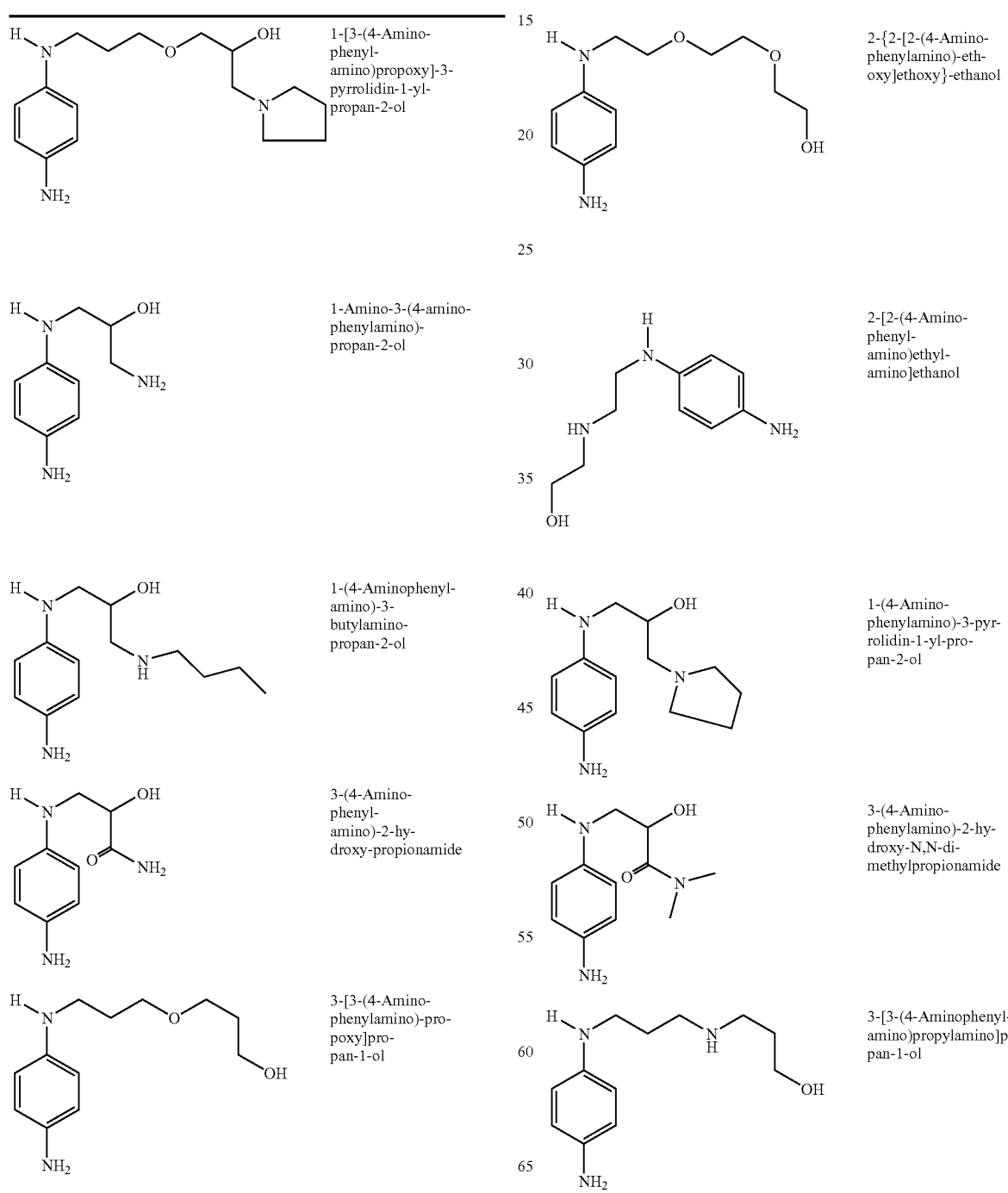

-continued

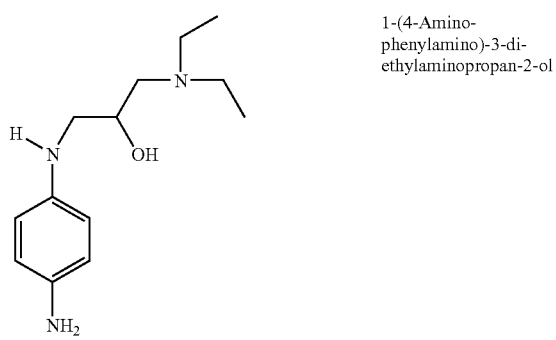

1-(4-Amino-phenylamino)-3-di-ethylaminopropan-2-ol

The compounds of formula (I) according to the present disclosure may be prepared according to a method including the following steps: production of a 4-(N-alkylhydroxylated) nitrobenzene compound by nucleophilic substitution of the halogen of a nitrobenzene compound substituted in the para position with a halogen, such as fluorine or chlorine, with a hydroxylated amine of formula HORNH$_2$ (R being as defined above) in the presence of a base, followed by reduction of the nitro group of the 4-(N-alkylhydroxylated)nitrobenzene compound obtained to give the N-alkylhydroxylated secondary para-phenylenediamine:

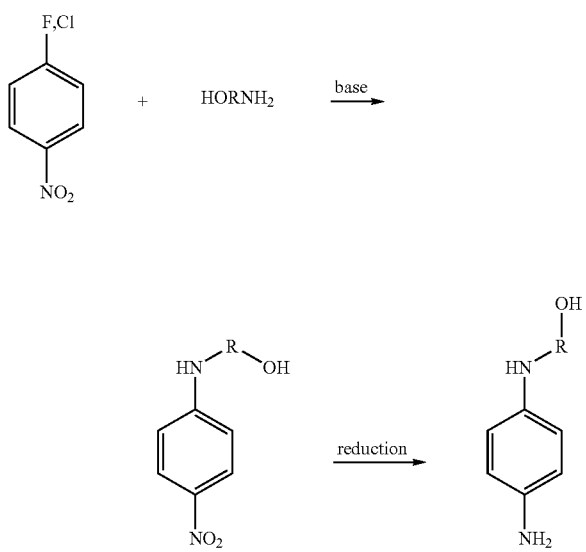

The first process of the synthesis is described in the documents Synthesis, 1990 (12), 1147-1148, and Synth. Commun., 1990, 20 (22), 3537-3543.

The second process is a standard reduction reaction, such as performing a hydrogenation reaction via heterogeneous catalysis in the presence of Pd/C, Pd(II)/C or Raney Ni, or alternatively by performing a reduction reaction with a metal, for example with zinc, iron, tin, etc. (Advanced Organic Chemistry, 4$^{th}$ edition, 1992, J. March, Wiley Interscience; Reduction in Organic Chemistry, M. Hudlicky, 1983, Ellis Honwood series Chemical Science).

The present disclosure also relates to the nitro compounds of formula (II):

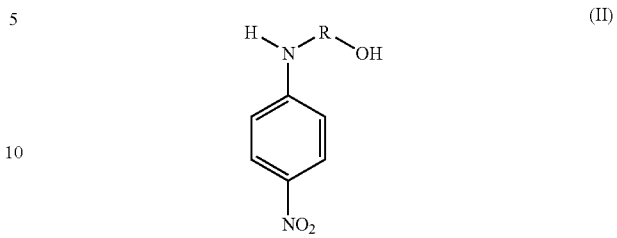

wherein:

R is a linear or branched $C_2$-$C_{14}$ alkylene radical substituted with one or more groups chosen from amino, monoalkylamino, dialkylamino, alkylcarbonyl, amido, monoalkylaminocarbonyl, dialkylaminocarbonyl, and saturated 5- or 6-membered heterocycles; or R is a linear or branched $C_2$-$C_{14}$ alkylene radical comprising one or more atoms chosen from nitrogen and oxygen, and optionally substituted with one or more groups chosen from amino, monoalkylamino, dialkylamino, alkylcarbonyl, amido, monoalkylaminocarbonyl, dialkylaminocarbonyl, and saturated 5- or 6-membered heterocycles, with the proviso that the compound of formula (II) is not N-(p-nitrophenyl)-2-hydroxy-1,3-diaminopropane or N-1-[(2-hydroxy-3-aminopropyl)]-4-nitro-1-aminobenzene.

Another aspect of the present disclosure relates to processes for preparing the ortho-substituted and/or meta-substituted N-alkylhydroxylated secondary para-phenylenediamine compounds of formula (I), in which a step of reduction of the corresponding nitro compound is performed, the "corresponding nitro compound" being the compound of formula (I) in which the amino group para to the NHROH group is replaced with a nitro group.

The present disclosure also relates to the uses of the compounds of formula (I) for dyeing keratin fibers, including human keratin fibers such as hair, with the proviso that the compound of formula (I) is not 4-amino-N-[β-(β'-hydroxyethoxy)ethyl]aniline.

Another aspect of the present disclosure is a cosmetic composition for dyeing fibers, including keratin fibers such as hair, comprising, in a medium that is suitable for dyeing, at least one compound of general formula (I), with the proviso that the compound of formula (I) is not 4-amino-N-[β-(β'-hydroxyethoxy)ethyl]aniline.

A further aspect of the present disclosure relates to a cosmetic composition for dyeing fibers, including keratin fibers such as hair, comprising, in a medium that is suitable for dyeing, at least one compound of formula (I) and at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

The present disclosure further relates to the use of a cosmetic composition for dyeing fibers, including keratin fibers such as the hair, comprising, in a medium that is suitable for dyeing, at least one compound of formula (I), with the exception that the compound of formula (I) is not 4-amino-N-[β-(β'-hydroxyethoxy)ethyl]aniline.

In one embodiment of the present disclosure, the compound of formula (I) is present in an amount ranging from 0.0001% to 20% by weight relative to the total weight of the composition, such as from 0.005% to 6% by weight relative to the total weight of the composition.

The medium that is suitable for dyeing advantageously comprises water or a mixture of water and at least one organic solvent. Among the organic solvents that may be used, non-limiting mention may be made, for example, of branched or unbranched $C_1$-$C_4$ lower alcohols, such as ethanol and isopropanol; polyols and polyol ethers, such as 2-butoxyethanol, propylene glycol, propylene glycol monomethyl ether, diethylene glycol monomethyl ether and monoethyl ether, and glycerol; and aromatic alcohols such as benzyl alcohol or phenoxyethanol, and mixtures thereof.

In another aspect of the present disclosure, the cosmetic composition may comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

The above adjuvants can each be present in an amount ranging from 0.01% to 20% by weight relative to the total weight of the composition.

The composition according to the present disclosure may also comprise at least one additional oxidation dye precursor other than the compounds of formula (I), such as an oxidation coupler.

Among the oxidation couplers that may be used, non-limiting mention may be made of meta-phenylenediamines, meta-aminophenols, meta-diphenols, naphthalene-based couplers and heterocyclic couplers, and also the addition salts thereof.

Non-limiting examples of oxidation couplers that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

In one embodiment of the present disclosure, the at least one oxidation coupler is present in an amount ranging from 0.0001% to 20% by weight relative to the total weight of the composition, such as from 0.005% to 6% by weight relative to the total weight of the composition.

In another aspect of the present disclosure, the composition may contain at least one additional oxidation base other than the compound of formula (I).

In one embodiment of the present disclosure, the additional oxidation bases other than the compounds of formula (I) may be chosen from para-phenylenediamines, bis(phenyl)alkylenediamines, para-aminophenols, ortho-amino phenols and heterocyclic bases, and the addition salts thereof.

Among the para-phenylenediamines that may be used, non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and 6-(4-aminophenylamino)hexan-1-ol, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the acid addition salts thereof with an acid.

Among the bis(phenyl)alkylenediamines that may be used, non-limiting mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Among the para-aminophenols that may be used, non-limiting mention may be made, by way of example, of para-aminophenol, 4-amino-2-methylphenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl]-2-methylphenol and bis(5'-amino-2'-hydroxy)phenylmethane and the acid addition salts thereof.

Among the ortho-aminophenols that may be used, non-limiting mention may be made, by way of example, of 2-aminophenol, 2-amino-5-methylphenol, 2-amino-6-methylphenol and 5-acetamido-2-aminophenol, and the acid addition salts thereof.

Among the heterocyclic bases that may be used, non-limiting mention may be made, by way of example, of pyridine derivatives, pyrimidine derivatives and pyrazole derivatives.

Among the pyridine derivatives that may be used, non-limiting mention may be made of the compounds described, for example, in British Patent Nos. GB 1026978 and GB 1153196, as well as 2,5-diaminopyridine, 2-(4-methoxyphenyl)amino-3-aminopyridine, and 3,4-diaminopyridine, and the acid addition salts thereof.

Other pyridine oxidation bases that can be used in the present disclosure include the 3-aminopyrazolo[1,5-a]pyridine oxidation bases or the addition salts thereof described, for example, in French Patent Application FR 2 801 308. Non-limiting examples that may be mentioned include pyrazolo[1,5-a]pyrid-3-ylamine; 2-acetylaminopyrazolo-[1,5-a]pyrid-3-ylamine; 2-morpholin-4-ylpyrazolo[1,5-a]pyrid-3-ylamine; 3-aminopyrazolo-[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo[1,5-a]pyrid-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the acid addition salts thereof.

Among the pyrimidine derivatives that may be used, non-limiting mention may be made of the compounds described, for example, in German Patent No. DE 2359399; Japanese Patent Nos. JP 88-169571 and JP 05-63124; European Patent No. EP 0 770 375 or Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine and the addition salts thereof and the tautomeric forms thereof, when a tautomeric equilibrium exists.

Among the pyrazole derivatives that may be used, non-limiting mention may be made of the compounds described in German Patent Nos. DE 3843892 and DE 4133957; Patent Application Nos. WO 94/08969 and WO 94/08970; French Application No. FR-A-2 733 749; and German Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

In one embodiment of the present disclosure, the at least one oxidation base is present in an amount ranging from 0.0001% to 20% by weight relative to the total weight of the composition, such as from 0.005% to 6% by weight relative to the total weight of the composition.

In one aspect of the present disclosure, the addition salts of the oxidation bases and oxidation couplers that may be used can be chosen from the addition salts with an acid such as the hydrochlorides, hydrobromides, sulfates, citrates, succinates, tartrates, lactates, tosylates, benzenesulfonates, phosphates and acetates.

The dye composition in accordance with the present disclosure may also comprise at least one direct dye, which may be chosen from neutral, acidic or cationic nitrobenzene dyes; neutral, acidic or cationic azo direct dyes; neutral, acidic or cationic quinone or anthraquinone direct dyes; azine direct dyes; methine direct dyes; azomethine direct dyes; triarylmethane direct dyes; indoamine direct dyes; and natural direct dyes. In one embodiment, the composition according to the present disclosure comprises at least one dye chosen from cationic direct dyes and natural direct dyes.

Among the cationic direct dyes that may be used according to the present disclosure, non-limiting mention may be made of the cationic azo direct dyes described in Patent Application Nos. WO 95/15144 and WO 95/01772, and European Patent Application No. EP 714 954.

Among these cationic azo direct dyes, further non-limiting mention may be made of the following dyes:

1,3-dimethyl-2-[[4-(dimethylamino)phenyl]azo]-1H-imidazolium chloride;

1,3-dimethyl-2-[(4-aminophenyl)azo]-1H-imidazolium chloride; and 1-methyl-4-[(methylphenylhydrazono)methyl]pyridinium methyl sulfate.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. Further non-limiting mention may be made to the use of extracts or decoctions containing these natural dyes and also henna-based poultices or extracts.

The at least one direct dyecan be present in an amount ranging from 0.001% to 20% by weight relative to the total weight of the composition, such as from 0.005% to 10% by weight relative to the total weight of the composition.

A person skilled in the art will take care to select the adjuvants, additional oxidation dye precursors and direct dyes such that the beneficial properties associated with the oxidation dye composition in accordance with the present disclosure are not, or are not substantially, adversely affected by the envisaged addition(s).

The pH of the dye composition in accordance with the present disclosure may range from 3 to 12, for instance, from 5 and 11. The pH may be adjusted to the desired value using acidifying or basifying agents usually used in the dyeing of keratin fibers, or alternatively using standard buffer systems.

Among the acidifying agents that may be used, non-limiting mention may be made, for example, of mineral or organic acids other than carboxylic diacids, such as hydrochloric acid, orthophosphoric acid, sulfuric acid, carboxylic acids such as acetic acid, tartaric acid, citric acid and lactic acid, and sulfonic acids.

Among the basifying agents that may be used, non-limiting mention may be made, for example, of aqueous ammonia, alkali metal carbonates, alkanolamines such as monoethanolamine, diethanolamine and triethanolamine and also derivatives thereof, sodium hydroxide, potassium hydroxide and the compounds of formula (III):

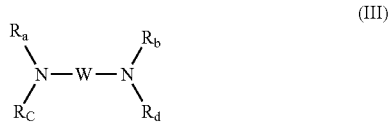

wherein W is a propylene residue optionally substituted with a hydroxyl group or a $C_1$-$C_4$ alkyl radical; $R_a$, $R_b$, $R_c$ and $R_d$, which may be identical or different, are chosen from a hydrogen atom, a $C_1$-$C_4$ alkyl and $C_1$-$C_4$ hydroxyalkyl radical.

The cosmetic composition according to the present disclosure may be in various forms, such as in the form of liquids, creams or gels, or in any other form that is suitable for dyeing keratin fibers, such as human hair.

A further aspect of the present disclosure relates to a process in which the composition disclosed herein is applied to keratin fibers for a time sufficient to develop a desired coloration in the presence of an oxidizing agent, the oxidizing agent being applied before, simultaneously with or after the composition. The color may be revealed at acidic, neutral or alkaline pH and the oxidizing agent may be added to the composition disclosed herein just at the time of use, or the oxidizing agent may be used starting with an oxidizing composition containing it, which is applied simultaneously with or sequentially to the composition.

According to one embodiment of the composition of the present disclosure, the dye composition is mixed, such as at the time of use, with a composition comprising, in a medium that is suitable for dyeing, at least one oxidizing agent, this oxidizing agent being present in an amount that is sufficient to develop a coloration.

According to a further embodiment, a ready-to-use composition is provided, which is a mixture of a composition according to the present disclosure with at least one oxidizing agent chosen from hydrogen peroxide, urea peroxide, alkali metal bromates, persalts, peracids and oxidase enzymes. The mixture obtained, in the form of a ready-to-use composition, can be applied to keratin fibers for a time that is sufficient to develop the desired coloration. After an action time of from 3 to 50 minutes, such as 5 to 30 minutes, the keratin fibers can be rinsed, washed with shampoo, rinsed again and then dried.

The oxidizing agents conventionally used for the oxidation dyeing of keratin fibers are chosen from, for example, hydrogen peroxide, urea peroxide, alkali metal bromates, persalts such as perborates and persulfates, peracids and oxidase enzymes, among which non-limiting mention may be made of peroxidases, two-electron oxidoreductases such as uricases, and four-electron oxygenases, such as laccases. In one embodiment of the present disclosure, hydrogen peroxide is used as the oxidizing agent.

The oxidizing composition may also contain various adjuvants conventionally used in hair dye compositions and as disclosed herein.

The pH of the oxidizing composition comprising the oxidizing agent can be such that, after mixing with the dye composition, the pH of the resulting composition applied to the keratin fibers ranges from 3 to 12, such as from 5 and 11.

The pH may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, such as human hair.

An additional aspect of the present disclosure relates to a multi-compartment device or dyeing "kit", in which a first compartment comprises the dye composition disclosed herein and a second compartment comprises an oxidizing composition. The kit may be equipped with an applicator for applying the desired mixture to the hair, such as the devices described in French Patent No. FR-2 586 913.

Using this kit, it is possible to dye keratin fibers via a process that includes mixing a dye composition in accordance with the invention with an oxidizing agent as defined above, and applying the mixture obtained to the keratin fibers for a time that is sufficient to develop the desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurement.

The following examples are intended to illustrate the invention in a non-limiting manner.

EXAMPLES

Example 1 synthesis of
2-[2-(4-aminophenylamino)ethylamino]ethanol
dihydrochloride (2)

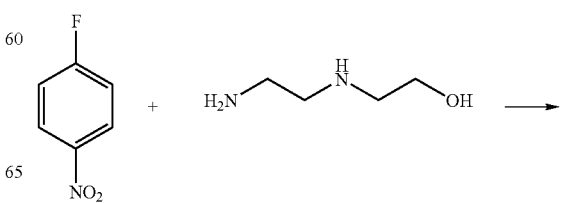

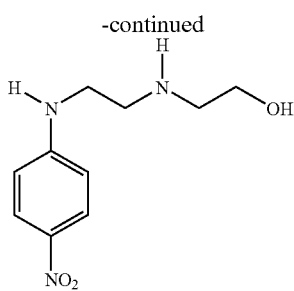

1

Step 1: synthesis of
2-[2-(4-nitrophenylamino)ethylamino]ethanol (1)

6 g of 4-fluoronitrobenzene and 10 g of 2-(2-aminoethylamino)ethanol were added to a solution of 100 ml of N-methylpyrrolidinone. The reaction medium was heated at 60° C. for 4 hours and, after cooling to room temperature, was then poured into a water and ice mixture. The yellow precipitate formed was filtered off, reslurried in water and then dried over $P_2O_5$. 8.88 g of 2-[2-(4-nitrophenylamino)ethylamino]ethanol (1) were obtained.

Step 2: Synthesis of
2-[2-(4-aminophenylamino)ethylamino]ethanol
dihydrochloride (2)

The 2-[2-(4-nitrophenylamino)ethylamino]ethanol (1) obtained above was reduced with a boiling zinc/ammonium chloride/water/ethanol mixture. The corresponding amine was isolated in dihydrochloride form.

The proton NMR and mass spectra were in accordance with the expected structure of the product.

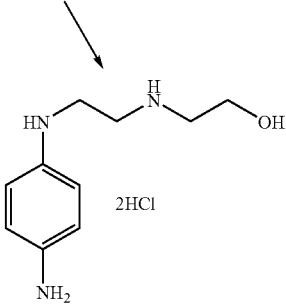

2

EXAMPLES OF DYEING

Examples 1 to 7

Dye composition using
2[2-(4-aminophenylamino)ethylamino]-ethanol
dihydrochloride (2)

Examples 1 to 7: Dyeing in Acidic Medium

The following dye compositions were prepared:

|  | Example | | | | | | |
|---|---|---|---|---|---|---|---|
|  | 1 | 2 | 3 | 4 | 5 | 6 | 7 |
| 2-[2-(4-Aminophenylamino)-ethyl-amino]ethanol dihydrochloride (2) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6%.by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

| | Example | | | | | | |
|---|---|---|---|---|---|---|---|
| | 1 | 2 | 3 | 4 | 5 | 6 | 7 |
| Shade observed | orange | orange | strong orange-brown | orange | orange | strong grey | orange |

What is claimed is:

1. An N-alkylhydroxylated secondary para-phenylenediamine compound of formula (I) and the addition salts thereof:

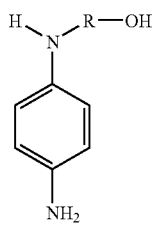

(I)

wherein:
R is chosen from linear and branched $C_2$-$C_{14}$ alkylene radicals substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5-or 6-membered heterocycles; and linear or branched $C_2$-$C_{14}$ alkylene radicals interrupted by one or more entities chosen from —NH— and oxygen, and optionally substituted with at least one group chosen from amino, monoalkylamino, dialkylamino, alkylcarbonyl, amido, monoalkylaminocarbonyl, dialkylaminocarbonyl, and saturated 5-or 6-membered heterocycles;

wherein the compound of formula (I) is not 4-amino-N-[β-(β'-hydroxyethoxy)ethyl]aniline.

2. The compound according to claim 1, wherein R is chosen from linear and branched $C_2$-$C_8$ alkylene radicals substituted with a group chosen from $C_1$-$C_{10}$ alkoxy, amino, $C_1$-$C_3$ monoalkylamino, $C_1$-$C_3$ dialkylamino, amido, di($C_1$-$C_3$) alkylaminocarbonyl, and saturated 5-or 6-membered heterocycles comprising a nitrogen atom.

3. The compound according to claim 1, wherein R is a linear $C_2$-$C_6$ alkylene radical interrupted by one or two entities chosen from —NH— and oxygen.

4. The compound according to claim 1, wherein R is a linear or branched $C_2$-$C_8$ alkylene radical interrupted by one or more entities chosen from —NH— and oxygen and substituted with a group chosen from $C_1$-$C_3$ alkylamino, $C_1$-$C_3$ dialkylamino, and saturated 5-or 6-membered heterocycles comprising a nitrogen atom.

5. The compound according to claim 1, wherein the compound is in the form of an addition salt.

6. The compound according to claim 5, wherein the compound is in the form of an addition salt with an acid chosen from hydrochlorides, hydrobromides, sulfates, citrates, succinates, tartrates, lactates, tosylates, benzenesulfonates, phosphates, and acetates.

7. The compound according to claim 1, wherein the compound is chosen from 1-[3-(4-aminophenylamino)propoxy]-3-pyrrolidin-1-ylpropan-2-ol; 2-[2-(4-aminophenylamino)ethylamino]ethanol; 1-amino-3-(4-aminophenylamino)propan-2-ol; 1-(4-aminophenylamino)-3-butylaminopropan-2-ol; 1-(4-aminophenylamino)-3-pyrrolidin-1-ylpropan-2-ol; 3-(4-aminophenylamino)-2-hydroxypropionamide; 3-(4-aminophenylamino)-2-hydroxy-N,N-dimethylpropionamide; 3-[3-(4-aminophenylamino)propoxy]propan-1-ol; 3-[3-(4-aminophenylamino)propylamino]propan-1-ol; 1-[3-(4-amino-phenylamino)propoxy]-3-diethylaminopropan-2-ol; 2-{2-[2-(4-amino,phenylamino)ethoxy]ethoxy}ethanol; and 1-(4-aminophenylamino)-3-diethylaminopropan-2-ol.

8. A nitro compound of formula (II) and the addition salts thereof:

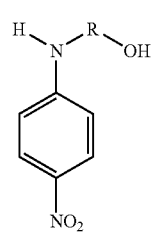

(II)

wherein:
R is chosen from linear and branched $C_2$-$C_{14}$ alkylene radicals substituted with at least one group chosen from amino, monoalkylamino, dialkylamino, alkylcarbonyl, amido, monoalkylaminocarbonyl, dialkylaminocarbonyl, and saturated 5-or 6-membered heterocycles; and linear and branched $C_2$-$C_{14}$ alkylene radicals interrupted by one or more entities chosen from —NH— and oxygen, and optionally substituted with one or more groups chosen from amino, monoalkylamino, dialkylamino, alkylcarbonyl, amido, monoalkylaminocarbonyl, dialkylaminocarbonyl, and saturated 5- or 6-membered heterocycles;

wherein the nitro compound of formula (II) is not N-(p-nitrophenyl)-2-hydroxy-1,3-diaminopropane and of N-1-[(2-hydroxy-3-aminopropyl)]-4-nitro-1-aminobenzene.

9. . A process for preparing an N-alkylhydroxylated secondary para-phenylenediamine compound of formula (I), comprising reducing a nitro compound to give the compound of formula (I) and addition salts thereof:

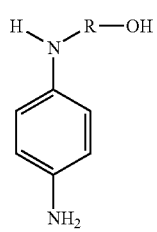

wherein:

R is chosen from linear and branched $C_2$-$C_{14}$ alkylene radicals substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5- or 6-membered heterocycles; and linear and branched $C_2$-$C_{14}$ alkylene radicals interrupted by one or more entities chosen from —NH— and oxygen, and optionally substituted with at least one group chosen from amino, monoalkylamino, dialkylamino, alkylcarbonyl, amido, monoalkylaminocarbonyl, dialkylaminocarbonyl, and saturated 5- or 6-membered heterocycles;

wherein the compound of formula (I) is not 4-amino-N-[β-(β'-hydroxyethoxy)ethyl]aniline.

10. A composition for dyeing keratin fibers comprising, in a medium that is suitable for dyeing, at least one N-alkylhydroxylated secondary para-phenylenediamine compound of formula (I) and the addition salts thereof,

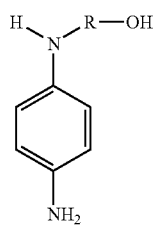

wherein:

R is chosen from linear and branched $C_2$-$C_{14}$ alkylene radicals substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5- or 6-membered heterocycles; and linear and branched $C_2$-$C_{14}$ alkylene radicals interrupted by one or more entities chosen from —NH— and oxygen, and optionally substituted with at least one group chosen from amino, monoalkylamino, dialkylamino, alkylcarbonyl, amido, monoalkylaminocarbonyl, dialkylaminocarbonyl, and saturated 5- or 6-membered heterocycles;

wherein the compound of formula (I) is not 4-amino-N-[β-(β'-hydroxyethoxy)ethyl]aniline.

11. The composition according to claim 10, wherein the compound of formula (I) is present in an amount ranging from 0.0001% to 20% by weight relative to the total weight of the composition.

12. The composition according to claim 10, wherein the medium that is suitable for dyeing comprises water or a mixture of water and at least one organic solvent chosen from branched and unbranched $C_1$-$C_4$ lower alcohols, polyols and polyol ethers, and aromatic alcohols.

13. The composition according to claim 12, wherein the medium that is suitable for dyeing comprises a mixture of water and at least one organic solvent chosen from ethanol and isopropanol.

14. The composition according to claim 13, wherein the medium that is suitable for dyeing comprises a mixture of water and at least one organic solvent chosen from 2-butoxyethanol, propylene glycol, propylene glycol monomethyl ether diethylene glycol monomethyl ether, diethylene glycol monoethyl ether, and glycerol.

15. The composition according to claim 13, wherein the medium that is suitable for dyeing comprises a mixture of water and at least one organic solvent chosen from benzyl alcohol or phenoxyethanol.

16. The composition according to claim 10, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents or opacifiers, and vitamins or provitamins.

17. The composition according to claim 16, wherein each cosmetic adjuvant is present in an amount ranging from 0.01% to 20% by weight relative to the total weight of the composition.

18. The composition according to claim 10, wherein the composition further comprises at least one additional oxidation dye precursor other than the compounds of formula (I).

19. The composition according to claim 18, wherein the at least one additional oxidation dye precursor is an oxidation coupler chosen from meta-phenylenediamines, meta-aminophenols, meta-diphenols, naphthalene-based couplers and heterocyclic couplers, and the addition salts thereof.

20. The composition according to claim 19, wherein the oxidation coupler is present in an amount ranging from 0.0001% to 20% by weight relative to the total weight of the composition.

21. The composition according to claim 18, wherein the at least one additional oxidation dye precursor is an oxidation base other than the compounds of formula (I), chosen from para-phenylenediamines, bis(phenyl)alkylenediamines, para-aminophenols, ortho-aminophenols and heterocyclic bases, and the addition salts thereof.

22. The composition according to claim 21, wherein the oxidation base is present in an amount ranging from 0.0001% to 20% by weight relative to the total weight of the composition.

23. The composition according to claim 12, further comprising at least one natural or cationic direct dye.

24. A ready-to-use composition, comprising:
a dye composition comprising at least one N-alkylhydroxylated secondary para-phenylenediamine compound of formula (I) and the addition salts thereof,:

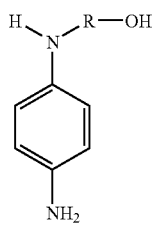

wherein:
R is chosen from linear and branched $C_2$-$C_{14}$ alkylene radicals substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5- or 6-membered heterocycles; and linear and branched $C_2$-$C_{14}$ alkylene radicals, interrupted by one or more entities chosen from —NH— and oxygen, and optionally substituted with at least one group chosen from amino, monoalkylamino, dialkylamino, alkylcarbonyl, amido, monoalkylaminocarbonyl, dialkylaminocarbonyl, and saturated 5- or 6-membered heterocycles;
wherein the compound of formula (I) is not 4-amino-N-[β-(β'-hydroxyethoxy)ethyl]aniline; and
at least one oxidizing agent chosen from hydrogen peroxide, urea peroxide, alkali metal bromates, persalts, peracids and oxidase enzymes.

25. A process for dyeing keratin fibers, comprising:
applying a dye composition to the fibers for a time sufficient to develop a desired coloration, in the presence of an oxidizing agent, the oxidizing agent being applied before, simultaneously with or after the dye composition is applied, wherein the dye composition comprises, in a medium suitable for dyeing keratin fibers, at least one N-alkylhydroxylated secondary para-phenylenediamine compound of formula (I) and the addition salts thereof,

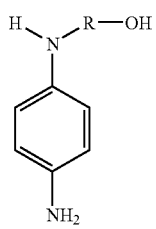

wherein:
R is chosen from linear and branched $C_2$-$C_{14}$ alkylene radicals substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5- or 6-membered heterocycles; and linear and branched $C_2$-$C_{14}$ alkylene radicals, interrupted by one or more entities chosen from —NH— and oxygen, and optionally substituted with at least one group chosen from amino, monoalkylamino, dialkylamino, alkylcarbonyl, amido, monoalkylaminocarbonyl, dialkylaminocarbonyl, and saturated 5- or 6-membered heterocycles;
wherein the compound of formula (I) is not of 4-amino-N-[β-(β'-hydroxyethoxy)ethyl]aniline.

26. The process of claim 25, wherein the oxidizing agent is chosen from hydrogen peroxide, urea peroxide, alkali metal bromates, persalts, peracids and oxidase enzymes.

27. A multi-compartment kit for dyeing keratin fibers comprising
a first compartment comprising a dye composition, comprising, in a medium suitable for dyeing keratin fibers, at least one N-alkylhydroxylated secondary para-phenylenediamine compound of formula (I) and the addition salts thereof,

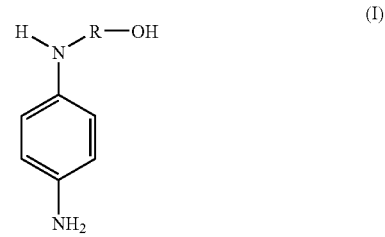

wherein:
R is chosen from linear and branched $C_2$-$C_{14}$ alkylene radicals substituted with at least one group chosen from $C_1$-$C_{10}$ alkoxy, amino, monoalkylamino, dialkylamino, alkylcarbonyl, amido, monoalkylaminocarbonyl, dialkylaminocarbonyl, and saturated 5- or 6-membered heterocycles; and linear or branched $C_2$-$C_{14}$ alkylene radicals interrupted by one or more entities chosen from —NH— and oxygen, and optionally substituted with at least one group chosen from amino, monoalkylamino, dialkylamino, alkylcarbonyl, amido, monoalkylaminocarbonyl, dialkylaminocarbonyl, and saturated 5- or 6-membered heterocycles;
wherein the compound of formula (I) is not of 4-amino-N-[β-(β'-hydroxyethoxy)ethyl]aniline; and
a second compartment comprising an oxidizing agent.

* * * * *

UNITED STATES PATENT AND TRADEMARK OFFICE
CERTIFICATE OF CORRECTION

PATENT NO. : 7,435,268 B2  Page 1 of 1
APPLICATION NO. : 11/066532
DATED : October 14, 2008
INVENTOR(S) : Stéphanie Sabelle et al.

It is certified that error appears in the above-identified patent and that said Letters Patent is hereby corrected as shown below:

In claim 1, column 15, line 52, "5-or" should read --5- or--.

In claim 1, column 15, line 58, "5-or" should read --5- or--.

In claim 2, column 15, line 66, "5-or" should read --5- or--.

In claim 4, column 16, line 8, "5-or" should read --5- or--.

In claim 7, column 16, lines 39-40, "1-[3-(4-amino-phenylamino)propoxy]-3-diethylaminopropan-2-ol;" should read --1-[3-(4-aminophenylamino)propoxy]-3-diethylaminopropan-2-ol;--.

In claim 7, column 16, lines 40-41, "2-{2-[2-(4-amino,phenylamino)ethoxy]ethoxy}ethanol;" should read --2-{2-[2-(4-aminophenylamino)ethoxy]ethoxy}ethanol;--.

In claim 8, column 16, line 63, "5-or" should read --5- or--.

In claim 8, column 17, lines 4-5, "N-(p-nitrophenyl)-2-hydroxy-1 ,3-diaminopropane" should read --N-(p-nitrophenyl)-2-hydroxy-1,3-diaminopropane--.

In claim 9, column 17, line 9, "9. . A" should read --9. A--.

In claim 24, column 19, line 4, "thereof,:" should read --thereof,--.

Signed and Sealed this

Second Day of December, 2008

JON W. DUDAS
*Director of the United States Patent and Trademark Office*